(12) United States Patent
Yue et al.

(10) Patent No.: US 11,940,367 B2
(45) Date of Patent: Mar. 26, 2024

(54) DEVICE FOR SIMULATING CARBON DIOXIDE STORAGE IN DEEP SALINE AQUIFER

(71) Applicant: Southwest Petroleum University, Chengdu (CN)

(72) Inventors: Ping Yue, Chengdu (CN); Hongnan Yang, Chengdu (CN); Yuan Lei, Chengdu (CN); Xu Zheng, Chengdu (CN); Peng Song, Chengdu (CN); Pengyu Chen, Chengdu (CN); Zhouhua Wang, Chengdu (CN); Simin Qu, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 0 days.

(21) Appl. No.: 18/501,936

(22) Filed: Nov. 3, 2023

(65) Prior Publication Data
US 2024/0068923 A1    Feb. 29, 2024

(30) Foreign Application Priority Data
Nov. 5, 2022    (CN) .......................... 202211380168.0

(51) Int. Cl.
*G01N 15/08*    (2006.01)
*G01N 33/24*    (2006.01)

(52) U.S. Cl.
CPC ......... *G01N 15/0806* (2013.01); *G01N 33/24* (2013.01)

(58) Field of Classification Search
CPC .... G01N 15/00; G01N 15/08; G01N 15/0806; G01N 33/24
See application file for complete search history.

(56) References Cited

U.S. PATENT DOCUMENTS

| | | | |
|---|---|---|---|
| 8,646,538 B2 * | 2/2014 | Baxter | E21B 41/0064 96/108 |
| 11,585,802 B1 * | 2/2023 | Qi | G01N 33/24 |

(Continued)

FOREIGN PATENT DOCUMENTS

| | | |
|---|---|---|
| CN | 103927913 A | 7/2014 |
| CN | 105424729 A | 3/2016 |

(Continued)

OTHER PUBLICATIONS

Simulation of CO2 Storage in Saline Aquifers; Ghanbari et al. Chemical Engineering Research and Design, 84(A9): 764-775 www.icheme.org/cherd; Institution of Chemical Engineers; Sep. 2006 (Year: 2006).*

*Primary Examiner* — Nguyen Q. Ha

(57) ABSTRACT

A device for simulating carbon dioxide storage in a deep saline aquifer, including a $CO_2$ gas source, first and second valves, first and second pressure pumps, first, second and third pressure gauges, a water storage tank, a simulation box, a first flow meter, a gas-liquid separator, a recycling tank, a microcomputer-display assembly, a structure plate, core holders, an injection pipeline, a connection pipeline, a baffle, a piezometer, a second flow meter, a heater, a lifter and an acoustic logging tool. The $CO_2$ gas source, the first valve, the first pressure pump and the first pressure gauge for gas injection. The water storage tank, a second pressure pump and a second pressure gauge for water injection. The second valve, the third pressure gauge, the first flow meter, the gas-liquid separator and the recycling tank form an output pipeline.

7 Claims, 6 Drawing Sheets

(56) References Cited

U.S. PATENT DOCUMENTS

2012/0211089 A1    8/2012  Piri
2023/0081834 A1*   3/2023  Smith ................ E21B 41/0064
                                                        423/220

FOREIGN PATENT DOCUMENTS

| CN | 111579463 A |   | 8/2020 |                    |
|----|-------------|---|--------|--------------------|
| CN | 114544461 A |   | 5/2022 |                    |
| CN | 115788578 A | * | 3/2023 | .............. E21F 17/16 |
| WO | WO-2023071552 A1 | * | 5/2023 | ............... G01N 5/00 |

* cited by examiner

DEVICE FOR SIMULATING CARBON DIOXIDE STORAGE IN DEEP SALINE AQUIFER

CROSS-REFERENCE TO RELATED APPLICATIONS

This application claims the benefit of priority from Chinese Patent Application No. 202211380168.0, filed on Nov. 5, 2022. The content of the aforementioned application, including any intervening amendments made thereto, is incorporated herein by reference in its entirety.

TECHNICAL FIELD

This application relates to carbon dioxide ($CO_2$) storage for mitigating the greenhouse gas emission, and more particularly to a device for simulating $CO_2$ storage in a deep saline aquifer.

BACKGROUND

The industrialization process has led to considerable greenhouse gas (e.g., $CO_2$) emissions, which further results in global warming and serious greenhouse issue. The main part of the global $CO_2$ emission is fossil fuel combustion, which is also the dominant energy supply means, and cannot be completely replaced in the next decade. If the global $CO_2$ emission cannot be effectively controlled, the total $CO_2$ emission will exceed 50 billion tons per year by 2050, which is a 50% increase over 2001. Therefore, it is necessary to take effective measures to carry out the global energy conservation and emission reduction and $CO_2$ storage.

CCS (Carbon Capture and Storage) technology refers to permanent storage for captured $CO_2$, which is different from natural carbon sequestration. In the CCS technology, a mature industrialized means is adopted to store the captured $CO_2$ underground for a long time or permanently. The alternative storage sites include oil/gas reservoirs, deep saline aquifer, deep sea, and unmineable coal seam. The CCS technology has advantages of high efficiency, long-term storage of $CO_2$ and high capacity, but it is required to pay attention to the risk of $CO_2$ leakage after storage. Advantages and disadvantages of several storage sites are summarized in Table 1.

TABLE 1

| Advantages and disadvantages of several storage sites | | |
|---|---|---|
| Storage site | Advantage(s) | Disadvantage(s) |
| Oil/Gas reservoir | The structural characteristics are determined, and the recovery of oil/gas reservoir can be improved; Related facilities are available; and High capacity (the mined reservoirs have large reserves). | It is required to analyze the applicability of the reservoir for storage, and the injection amount is limited by the development process; and It is produced with the produced fluid, and separation and reinjection are needed. |
| Unmineable coal seam | Improving the methane output | Not all coal seams are suitable for the $CO_2$ storage, and the storage capacity is relatively small. |
| Deep sea | $CO_2$ is dissolved into bicarbonates; and $CO_2$ is converted into stable hydrates. | Injection of excessive $CO_2$ will cause local pH change of seawater; and Dissolved $CO_2$ may escape in the presence of ocean currents and in supersaturated state. |
| Deep saline aquifer | High capacity; Wide distribution of optional deep saline aquifers; and Near the $CO_2$ emission source. | Unknown structural integrity; High monitoring difficulty; and Salting out is prone to occurring near the well in the case of excessive concentration. |

In the above-listed storage sites, the deep saline aquifer has attracted more and more attention because of its high storage capacity, wide distribution and low storage difficulty. At present, the depth of $CO_2$ storage in a deep saline aquifer is generally 1000~2000 m, because a small storage depth may cause pollution to surface water, and a large depth raises high requirement for the storage technology. At this time, the injected $CO_2$ is in a critical state because of high temperature and high pressure, and it also has the nature of gas and the flow ability of liquid. The supercritical $CO_2$ can float up and gather at the top after it is injected into the reservoir, owing to its low density (0.6 times the density of water) and low viscosity (0.05~0.1 times the viscosity of water). Finally, the supercritical $CO_2$ is accumulated under the cap rock under the action of plume, and viscous fingering and gravity differentiation appear. When the buoyance of $CO_2$ is greater than the capillary force in pores, the injected $CO_2$ enters the pores of the cap rock, which is easy to weaken the sealing of the cap rock and causes a risk of leakage after a long time.

Extensive attempts have been made to carbon dioxide capture and storage in the deep saline aquifer, such as France Nord project and Shenhua CCS demonstration project, and the first CCS pilot project with 1000 thousand tons per year in China has been built in the Shenhua CCS demonstration project (operated for about 3 years). However, there is still a lack of relevant research means in the field of carbon dioxide storage in the deep saline aquifer in China. It is important to simulate and monitor the migration and sequestration of carbon dioxide in stratums in the process of storage in a deep saline aquifer. In view of this, it is urgently needed to develop a device capable of simulating the whole process of structural storage, dissolution storage and mineralizing storage after carbon dioxide is injected into the deep saline aquifer.

An object of the present disclosure is to provide a modularized device to quantitatively study and monitor $CO_2$ storage in the deep saline aquifer.

SUMMARY

An object of the present disclosure is to provide a modularized device to quantitatively study and monitor storage of carbon dioxide in a deep saline aquifer.

Technical solutions of the present disclosure are described as follows.

This application provides a device for simulating carbon dioxide storage in a deep saline aquifer, comprising:

- a $CO_2$ gas source;
- a first valve;
- a second valve;
- a first pressure pump;
- a second pressure pump;
- a first pressure gauge;
- a second pressure gauge;
- a third pressure gauge;
- a water storage tank;
- a stimulation box;
- a first flow meter;
- a gas-liquid separator;
- a recycling tank;
- a microcomputer-display assembly;
- a structure plate;
- a plurality of core holders;
- an injection pipeline;
- a connection pipeline;
- a baffle;
- a piezometer;
- a second flow meter;
- a heater;
- a lifter; and
- an acoustic logging tool;
  wherein the $CO_2$ gas source, the first valve, the first pressure pump and the first pressure gauge are arranged on a first pipe for gas injection; the water storage tank, the second pressure pump and the second pressure gauge are arranged on a second pipe for water injection; and the second valve, the third pressure gauge, the first flow meter, the gas-liquid separator and the recycling tank are arranged on a third pipe to form an output pipeline; the stimulation box is connected to the first pressure gauge, the second pressure gauge and the second valve, and is located at a junction of the first pipe, the second pipe and the output pipeline; the microcomputer-display assembly is connected with the stimulation box and is configured to save and monitor injection rates of the first pressure pump and the second pressure pump and values of the piezometer, the second flow meter and the heater; the structure plate, the baffle, the heater, the lifter and the acoustic logging tool are arranged in the stimulation box to form an anticline structure with stable shape and temperature to monitor movement of a gas-water interface;
  the plurality of core holders, the connection pipeline and the injection pipeline are placed on the structure plate, and the plurality of core holders are fixed by the baffle to form the anticline structure; the structure plate, the baffle and the lifter are configured to work together to form a deep saline aquifer reservoir, which has an adjustment ability and is capable of simulating various structure forms; the injection pipeline is directly connected with the connection pipeline between the plurality of core holders to inject carbon dioxide gas into a top of the deep saline aquifer; the piezometer and the second flow meter are arranged on the connection pipeline between the plurality of core holders to monitor gas-water flow between the plurality core holders;
  each of the plurality of core holders is composed of a core holder body and a cover; a first end of the core holder body is non-detachably connected with the connection pipeline, and a second end of the core holder body is configured to enable tri-axial core holding, and is threadedly connected with the cover; the plurality of core holders are communicated with the connection pipeline so that the plurality of core holders have the same pressure; a first side of the simulation box is connected with the second pipe to maintain stable pressure inside the plurality of core holders, and a second side of the simulation box is connected with the output pipeline to discharge gas and liquid inside the simulation box; and the second valve, the third pressure gauge, the first flow meter, the gas-liquid separator and the recycling tank are arranged on a fourth pipe to separate and recycle a fluid produced in the simulation box; and
  in an embodiment, each of the plurality of core holders is a split-type columnar core holder; and the plurality core holders are connected through the connection pipeline, and are connected with the piezometer, the second flow meter and the injection pipeline through the connection pipeline.

In an embodiment, the structure plate and the lifter are configured to cooperate with each other to form various stratum structures. The lifter is configured to work independently to lift the structure plate, and to cooperate with the baffle to form the plurality core holders into various structure forms.

In an embodiment, the piezometer and the second flow meter on the connection pipeline are configured to monitor pressure changes and fluid flows inside the plurality of core holders at different positions on the structure plate. The microcomputer-display assembly is configured to display pressure data and flow data in real time. And the acoustic logging tool on the simulation box is configured to determine a position of a gas-liquid interface inside each of the core holders and monitor diffusion-convection route and range during injection and storage of $CO_2$ at different moment.

In an embodiment, the device is configured to calculate a volume of free $CO_2$ gas of in each of the plurality of core holders based on a position of the gas-liquid interface inside each of the plurality of core holders and an accumulative injection volume of $CO_2$, so as to calculate a volume of $CO_2$ dissolved in water.

In an embodiment, a core of each of the plurality of core holders can be removed. A dissolved volume of reaction between minerals in the core and $CO_2$ can be determined by drying and weighting the core. And contribution of capture of the minerals in the core to the whole $CO_2$ storage is determined based on a reduction of weight of the core.

In an embodiment, the plurality of core holders, the piezometer and the second flow meter are connected through the connection pipeline, and are placed on the structure plate to simulate the deep saline aquifer reservoir with the anticline structure.

In an embodiment, the injection pipeline and the plurality of core holders are directly connected with the connection pipeline, and a liquid is continuously supplied to the plurality of core holders and the connection pipeline through the water storage tank, the second pressure pump and the second pressure gauge to ensure constant pressure inside the plurality of core holders.

In an embodiment, the output pipeline is directly connected with the plurality of core holders on the second side of the simulation box and the connection pipeline, and the second valve is opened when the core is saturated with water; when the experiment starts, the second valve is closed to keep constant pressure of the device; and after the experiment, the second valve is opened to discharge the fluid inside the device.

In an embodiment, the simulation box is configured to accommodate the lifter, the structure plate, the baffle, the plurality of core holders, the connection pipeline, the heater, the acoustic logging tool and the injection pipeline. And the simulation box has the anticline structure formed by the structure plate and the lifter, and the plurality of core holders and the connection pipeline are placed in the anticline structure to simulate a structure for carbon dioxide storage in the deep saline aquifer.

In an embodiment, the microcomputer-display assembly is connected with the piezometer and the second flow meter inside the simulation box to display and save readings of the piezometer and the second flow meter.

The present disclosure has the following beneficial effects: (1) the device can monitor accumulation form and movement route of carbon dioxide storage in the deep saline aquifer because of geological structures; and fluid flow between the plurality of core holders can be obtained by the piezometer and the second flow meter; and the gas-water interface inside the plurality of core holders can be obtained by the acoustic logging tool; (2) a flexible combination of the structure plate and the lifter can form various geological structures to simulate geological storage effect of carbon dioxide at different inclination angles of stratums; and (3) the plurality of core holders use real cores saturated with formation water, which flow and dissolution of carbon dioxide in the deep saline aquifer are consistent with that underground, so that the experiment is reliable.

Figure 1:
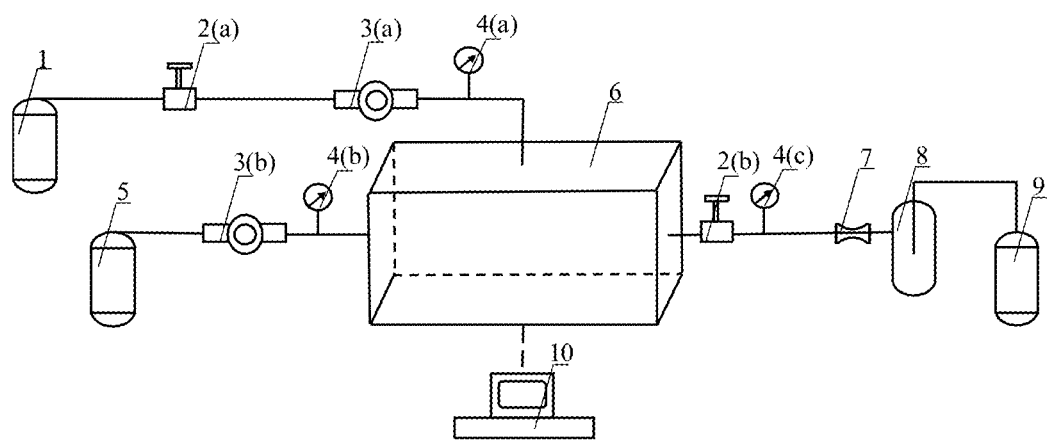
FIG. 1 is a structural diagram of a device for simulating carbon dioxide storage in a deep saline aquifer according to an embodiment of the present disclosure.

In the figures: $CO_2$ gas source 1, first valve 2a, second valve 2b, first pressure pump 3a, second pressure pump 3b, first pressure gauge 4a, second pressure gauge 4b, third pressure gauge 4c, water storage tank 5, simulation box 6, first flow meter 7, gas-liquid separator 8, recycling tank 9, microcomputer-display assembly 10, structure plate 11, core holder 12, injection pipeline 13, connection pipeline 14, baffle 15, piezometer 16, second flow meter 17, heater 18, lifter 19, core holder body 20, cover 21, and acoustic logging tool 22.

DETAILED DESCRIPTION OF EMBODIMENTS

The technical solutions of this application will be further described with reference to the embodiments and accompanying drawings.

Figure 2:
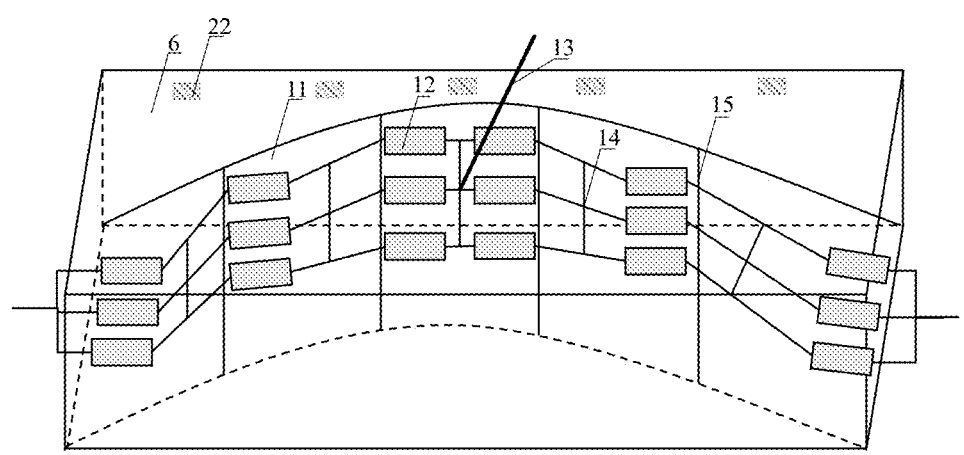
FIG. 2 shows a carbon dioxide storage device in a simulation box according to an embodiment of the present disclosure.
Figure 3:
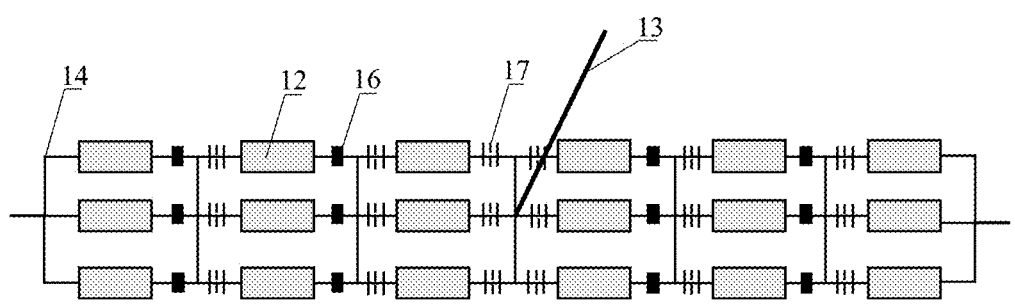
FIG. 3 is a plan illustrating seepage of the carbon dioxide storage according to an embodiment of the present disclosure.
Figure 4:
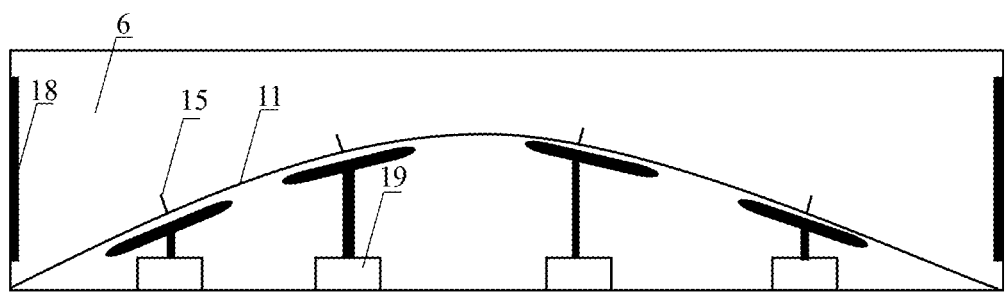
FIG. 4 is a cutaway view of an inside of a simulation box according to an embodiment of the present disclosure.
Figure 5:
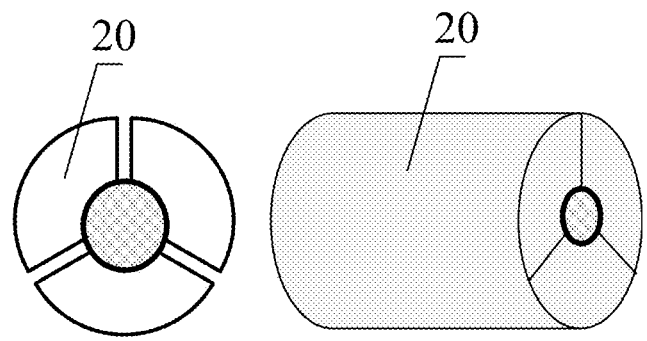
FIG. 5 is a structural diagram of a core holder body according to an embodiment of the present disclosure.
Figure 6:
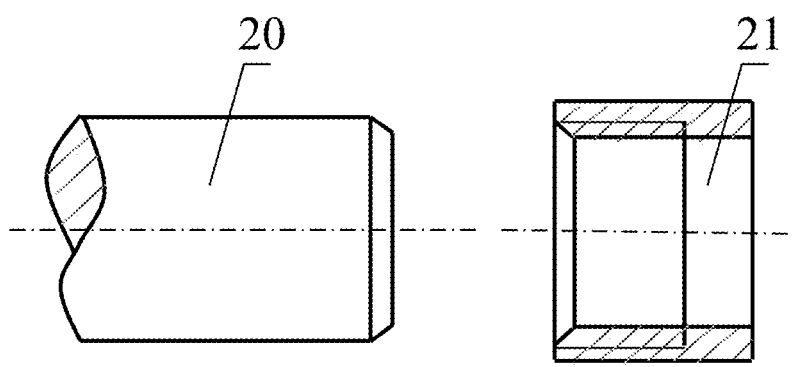
FIG. 6 shows assembly of the core holder body and a cover according to an embodiment of the present disclosure.

Referring to FIGS. 1-6, a device for simulating carbon dioxide storage in a deep saline aquifer is provided, including a $CO_2$ gas source 1, a first valve 2a, a second valve 2b, a first pressure pump 3a, a second pressure pump 3b, a first pressure gauge 4a, a second pressure gauge 4b, a third pressure gauge 4c, a water storage tank 5, a simulation box 6, a first flow meter 7, a gas-liquid separator 8, a recycling tank 9, a microcomputer-display assembly 10, a structure plate 11, a plurality of core holders 12, an injection pipeline 13, a connection pipeline 14, a baffle 15, a piezometer 16, a second flow meter 17, a heater 18, a lifter 19, a core holder body 20, a cover 21 and an acoustic logging tool 22. The $CO_2$ gas source 1, the first valve 2a, the first pressure pump 3a and the first pressure gauge 4a are arranged on a first pipe for gas injection. The water storage tank 5, the second pressure pump 3b and the second pressure gauge 4b are arranged on a second pipe for water injection. The second valve 2b, the third pressure gauge 4c, the first flow meter 7, the gas-liquid separator 8 and the recycling tank 9 are arranged on a third pipe to form an output pipeline. The stimulation box 6 is connected to the first pressure gauge 4a, the second pressure gauge 4b and the second valve 2b, and is located at a junction of the first pipe, the second pipe and the output pipeline; the microcomputer-display assembly 10 is connected with the stimulation box 6, and is configured to save and display injection rates of the first pressure pump 3a and the second pressure pump 3b and values of the piezometer 16, the second flow meter 17 and the heater 18. The structure plate 11, the baffle 15, the heater 18, the lifter 19 and the acoustic logging tool 22 are arranged in the stimulation box 6 to form a anticline structure with stable shape and temperature to monitor movement of a gas-water interface.

The plurality of core holders 12, the connection pipeline 14 and the injection pipeline 13 are placed on the structure plate 11, and the plurality of core holders 12 are fixed by the baffle 15. The lifter 19 is configured to lift the structure plate 11 to form the anticline structure. The injection pipeline 13 is directly connected with the connection pipeline 14 between the plurality of core holders 12 to inject carbon dioxide gas into a top of the deep saline aquifer. The piezometer 16 and the second flow meter 17 are arranged on the connection pipeline 14 between the plurality of core holders 12 to monitor gas-water flow between the plurality of core holders 12.

Each of the plurality of core holders 12 is composed of the core holder body 20 and the cover 21. A first end of the core holder body 20 is non-detachedly connected with the connection pipeline 14, and a second end of the core holder body 20 is configured to enable tri-axial core holding, and is threadedly connected with the cover 21. The plurality of core holders 12 are communicated with the connection pipeline 14 so that the plurality of core holders 12 have the same pressure. A first side of the simulation box 6 is connected with the second pipe to maintain stable pressure inside the plurality of core holders 12, and a second side of the simulation box 6 is connected with the output pipeline to discharge gas and liquid inside the simulation box 6. And the second valve 2b, the third pressure gauge 4c, the first flow meter 7, the gas-liquid separator 8 and the recycling tank 9 are arranged on a fourth pipe to separate and recycle a fluid produced in the simulation box 6.

Each of the plurality of core holders 12 is a split-type columnar core holder. And the plurality of core holders 12 are connected through the connection pipeline 14, and are connected with the piezometer 16, the second flow meter 17 and the injection pipeline 13 through the connection pipeline 14.

In an embodiment, the structure plate 11 and the lifter 19 are configured to cooperate with each other to form various stratum structures. The lifter 19 is configured to work independently to lift the structure plate 11, and to cooperate with the baffle 15 to fix the plurality of core holders 12 on the structure plate 11.

In an embodiment, the piezometer 16 and the second flow meter 17 on the connection pipeline 14 are configured to monitor pressure changes and fluid flows inside the plurality of core holders 12 at different positions on the structure plate 11. The microcomputer-displayer assembly 10 is configured to display pressure data and flow data in real time. The acoustic logging tool 22 on the simulation box 6 is configured to determine a position of the gas-liquid interface inside each of the plurality of core holders 12 and monitor diffusion-convection route and range during injection and storage of $CO_2$ at different moments.

In an embodiment, the device is configured to calculate a volume of free $CO_2$ gas in each of the plurality of core holders 12 through a position of the gas-liquid interface inside each of the plurality of core holders 12 and an accumulative injection volume of $CO_2$, so as to calculate a volume of $CO_2$ dissolved in water.

In an embodiment, a core of each of the plurality of core holders 12 can be removed. A dissolved volume of reaction between minerals in the core and $CO_2$ can be determined by drying and weighting the core. The contribution of capture of the minerals in the core to the whole $CO_2$ storage is determined based on the weight reduction of the core.

In an embodiment, the plurality of core holders 12, the piezometer 16 and the second flow meter 17 are connected through the connection pipeline 14, and are placed on the structure plate 11 to simulate the deep saline aquifer reservoir with the anticline structure.

In an embodiment, the injection pipeline 13 and the plurality of core holders 12 are directly connected with the connection pipeline 14, and a liquid is continuously supplied to the plurality of core holders 12 and the connection pipeline 14 through the water storage tank 5, the second pressure pump 3b and the second pressure gauge 4b to ensure constant pressure inside the core holder 12.

In an embodiment, the output pipeline is directly connected with the plurality of core holders 12 on a second side of the simulation box 6 and the connection pipeline 14, and the second valve 2b is opened when the core is saturated with water. When the experiment starts, the second valve 2b is closed to keep constant pressure of the simulation box 6. And after the experiment, the second valve 2b is opened to discharge the fluid inside the simulation box 6.

In an embodiment, the simulation box 6 is configured to accommodate the lifter 19, the structure plate 11, the baffle 15, the plurality of core holders 12, the connection pipeline 14, the heater 18, the acoustic logging tool 22 and the injection pipeline 13. And the simulation box 6 has the anticline structure formed by the structure plate 11 and the lifter 19, and the plurality of core holders 12, and the connection pipeline 14 are placed in the anticline structure to simulate a structure for carbon dioxide storage in the deep saline aquifer.

The microcomputer-display assembly 10 is connected with the piezometer 16 and the second flow meter 17 inside the simulation box 6 to display and save readings of the piezometer 16 and the flow meter 17.

What is claimed is:

1. A device for simulating carbon dioxide ($CO_2$) storage in a deep saline aquifer, comprising:
   a $CO_2$ gas source;
   a first valve;
   a second valve;
   a first pressure pump;
   a second pressure pump;
   a first pressure gauge;
   a second pressure gauge;
   a third pressure gauge;
   a water storage tank;
   a stimulation box;
   a first flow meter;
   a gas-liquid separator;
   a recycling tank;
   a microcomputer-display assembly;
   a structure plate;
   a plurality of core holders;
   an injection pipeline;
   a connection pipeline;
   a baffle;
   a piezometer;
   a second flow meter;
   a heater;
   a lifter; and
   an acoustic logging tool;
   wherein the $CO_2$ gas source, the first valve, the first pressure pump and the first pressure gauge are arranged on a first pipe for gas injection; the water storage tank, the second pressure pump and the second pressure gauge are arranged on a second pipe for water injection; and the second valve, the third pressure gauge, the first flow meter, the gas-liquid separator and the recycling tank are arranged on a third pipe to form an output pipeline; the stimulation box is connected to the first pressure gauge, the second pressure gauge and the second valve, and is located at a junction of the first pipe, the second pipe and the output pipeline; the microcomputer-display assembly is connected with the stimulation box, and is configured to save and display injection rates of the first pressure pump and the second pressure pump and values of the piezometer, the second flow meter and the heater; the structure plate, the baffle, the heater, the lifter and the acoustic logging tool are arranged in the stimulation box to form an anticline structure with stable shape and temperature to monitor movement of a gas-water interface;
   the plurality of core holders, the connection pipeline and the injection pipeline are placed on the structure plate, and the plurality of core holders are fixed by the baffle; the lifter is configured to lift the structure plate to form the anticline structure; the lifter has an independent adjustment ability, and is capable of simulating various structural forms; the injection pipeline is directly connected with the connection pipeline between the plurality of core holders to inject carbon dioxide gas into a top of the deep saline aquifer; the piezometer and the second flow meter are arranged on the connection pipeline between the plurality of core holders to monitor gas-water flow between the plurality of core holders; and each of the plurality of core holders is composed of a core holder body and a cover; a first end of the core holder body is non-detachably connected with the connection pipeline, and a second end of the core holder body is configured to enable tri-axial core holding, and is threadedly connected with the cover; the plurality of core holders are communicated with the connection pipeline so that the plurality of core holders have the same pressure; a first side of the simulation box is connected with the second pipe to maintain stable pressure inside the plurality of core holders, and a second side of the simulation box is connected with the output pipeline to discharge gas and liquid inside the simulation box; and the second valve, the third pressure gauge, the first flow meter, the gas-liquid separator and the recycling tank are arranged on a fourth pipe to separate and recycle a fluid produced in the simulation box.

2. The device of claim 1, wherein each of the plurality of core holders is a split-type columnar core holder; and the plurality of core holders are connected through the connection pipeline, and are connected with the piezometer, the second flow meter and the injection pipeline through the connection pipeline.

3. The device of claim 1, wherein the structure plate and the lifter are configured to cooperate with each other to form various stratum structures; and the lifter is configured to work independently to lift the structure plate, and to cooperate with the baffle to fix the plurality of core holders on the structure plate.

4. The device of claim 1, wherein the piezometer and the second flow meter on the connection pipeline are configured to monitor pressure changes and fluid flows inside the plurality of core holders at different positions on the structure plate; the microcomputer-display assembly is configured to display pressure data and flow data in real time; and the acoustic logging tool on the simulation box is configured to determine a position of a gas-liquid interface inside each of the plurality of core holders and monitor diffusion-convection route and range during injection and storage of $CO_2$ at different moments.

5. The device of claim 1, wherein the device is configured to calculate a volume of free $CO_2$ gas in each of the plurality of core holders based on a position of the gas-liquid interface inside each of the plurality of core holders and an accumulative injection volume of $CO_2$, so as to calculate a volume of $CO_2$ dissolved in water.

6. The device of claim 1, wherein the injection pipeline and the plurality of core holders are directly connected with the connection pipeline, and a liquid is continuously supplied to the plurality of core holders and the connection pipeline through the water storage tank, the second pressure pump and the second pressure gauge to ensure constant pressure inside the plurality of core holders.

7. The device of claim 1, wherein the simulation box is configured to accommodate the lifter, the structure plate, the baffle, the plurality of core holders, the connection pipeline, the heater, the acoustic logging tool and the injection pipeline; and the simulation box has the anticline structure formed by the structure plate and the lifter, and the plurality of core holders and the connection pipeline are placed in the anticline structure to simulate a structure for carbon dioxide storage in the deep saline aquifer.

* * * * *